(12) United States Patent
Suda et al.

(10) Patent No.: US 6,495,627 B1
(45) Date of Patent: *Dec. 17, 2002

(54) CONDUCTIVE COMPOSITION FOR BIOLOGICAL ELECTRODE

(75) Inventors: Shin Suda, Tokyo (JP); Tohru Kurata, Tokyo (JP)

(73) Assignee: Nihon Kohden Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/678,178

(22) Filed: Jul. 11, 1996

(30) Foreign Application Priority Data

Jul. 11, 1995 (JP) ............................. 7-174749
Jul. 11, 1995 (JP) ............................. 7-174750

(51) Int. Cl.$^7$ ............................. C08K 5/16; C08K 5/19; C08K 5/21
(52) U.S. Cl. ............................. 524/728; 522/8; 522/12; 522/18; 522/39; 522/42; 522/46; 522/64; 522/78; 522/79; 522/80; 522/175; 522/178; 522/182; 524/779; 524/714; 524/723; 524/724; 524/726; 524/755; 524/761; 524/762; 524/765; 524/767; 524/796; 524/766
(58) Field of Search ............................. 524/728, 729, 524/759, 761, 718, 700, 714, 779, 765, 755, 767, 766, 777, 762, 773, 723, 775, 724, 726, 796; 522/8, 12, 18, 39, 42, 46, 64, 78, 79, 80, 175, 178, 182

(56) References Cited

U.S. PATENT DOCUMENTS

| | | | | |
|---|---|---|---|---|
| 3,622,533 A | * | 11/1971 | O'Connor ............ 260/29.6 N |
| 3,857,991 A | * | 12/1974 | Higashimura et al. ........ 174/6 |
| 4,189,370 A | | 2/1980 | Boschetti |
| 4,474,570 A | * | 10/1984 | Ariura et al. .............. 604/20 |
| 4,581,821 A | | 4/1986 | Cahalan et al. ............. 29/877 |
| 4,657,656 A | * | 4/1987 | Ogawa et al. .......... 204/299 R |
| 4,666,707 A | * | 5/1987 | Eguchi et al. .............. 424/44 |
| 4,674,512 A | * | 6/1987 | Rolf ........................ 128/640 |
| 4,699,146 A | * | 10/1987 | Sieverding ............... 128/640 |
| 4,769,408 A | * | 9/1988 | Ogawa et al. ............ 524/156 |
| 4,842,577 A | * | 6/1989 | Konno et al. ............... 604/20 |
| 4,842,768 A | * | 6/1989 | Nakao et al. .............. 252/500 |
| 4,848,353 A | * | 7/1989 | Engel ....................... 128/640 |
| 4,851,434 A | * | 7/1989 | Deckner ................... 514/847 |
| 4,947,847 A | * | 8/1990 | Nakao et al. .............. 128/640 |
| 4,950,708 A | * | 8/1990 | Hochstrasser ............. 524/728 |
| 5,002,760 A | * | 3/1991 | Katzev ....................... 424/59 |
| 5,042,144 A | * | 8/1991 | Shimada et al. ............. 29/825 |
| 5,055,517 A | * | 10/1991 | Shorr et al. ................ 524/845 |
| 5,124,076 A | * | 6/1992 | Smuckler ................... 252/518 |
| 5,143,071 A | * | 9/1992 | Keusch et al. ............. 128/640 |
| 5,169,622 A | * | 12/1992 | Kopolow et al. ............. 424/47 |
| 5,219,923 A | * | 6/1993 | Shorr ........................ 524/827 |
| 5,225,473 A | * | 7/1993 | Duan ........................ 524/388 |
| 5,264,471 A | * | 11/1993 | Chmelir ...................... 524/35 |
| 5,354,790 A | * | 10/1994 | Keusch et al. ............. 523/300 |
| 5,385,729 A | * | 1/1995 | Prencipe et al. ......... 424/70.11 |
| 5,405,366 A | * | 4/1995 | Fox et al. ................... 607/50 |
| 5,456,701 A | * | 10/1995 | Stout ........................ 607/104 |
| 5,536,768 A | * | 7/1996 | Kanter et al. .............. 524/376 |
| 5,599,800 A | * | 2/1997 | Candau et al. .............. 514/53 |
| 5,622,168 A | * | 4/1997 | Keusch et al. ............. 128/640 |
| 5,660,178 A | * | 8/1997 | Kanter et al. .............. 128/640 |
| 5,665,477 A | * | 9/1997 | Meathrel et al. ........... 428/500 |

FOREIGN PATENT DOCUMENTS

| | | |
|---|---|---|
| JP | 6343646 | 2/1988 |
| JP | 6359334 | 11/1988 |
| JP | 232892 | 7/1990 |

* cited by examiner

Primary Examiner—Judy M. Reddick
(74) Attorney, Agent, or Firm—Sughrue Mion, PLLC

(57) ABSTRACT

A conductive composition for a biological electrode is capable of reducing the impedance between the electrode and the skin. A conductive gel composition for a biological electrode which is capable of electrically and physically connecting a living body to an electrode element and is composed of at least the following components: (1) a radical-polymerizable unsaturated compound; (2) a moisturizer serving as a plasticizer and functioning to supplementing and promoting the physiological humidifying function of the horny layer; (3) a polymerization initiator; and (4) a crosslinking agent. This moisturizer serves also as a plasticizer and, furthermore, elevates the moisture content in the horny layer at the application of this composition. The above-mentioned composition may further contain a plasticizer selected from among polyhydric alcohols, amines and ethers.

15 Claims, 1 Drawing Sheet

CONDUCTIVE COMPOSITION FOR BIOLOGICAL ELECTRODE

FIELD OF THE INVENTION

This invention relates to a conductive composition to be located between the skin and an electrode element when a biological electrode is applied to the skin.

BACKGROUND OF THE INVENTION

A biological electrode consists of an electrode element made of silver, silver/silver chloride, carbon and the like and a conductive composition connecting the electrode element to the skin and is applied to the surface of a living body in order to output some bioelectrical phenomena (e.g., electrocardiogram, electromyogram, etc.) or electrically stimulate the living body.

Normal human skin has an external layer called "horny layer" which protects the living body against the invasion of various foreign factors. When the skin is contacted with the dry atmosphere, the moisture is lost from the horny layer. Also, the moisture content in the horny layer is reduced as aging proceeds. In such cases, the electrical resistance of the horny layer is elevated. The surface of the skin is not smooth but uneven and has a complicated shape, for example, being curved.

When an electrode element is contacted directly with the skin surface containing less moisture in the horny layer, it is frequently observed that the contact of the electrode element to the skin is inhibited and thus the effective contact area is reduced. As a result, the contact resistance is elevated. In addition, the resistance of the horny layer per se has been elevated as described above. Thus the total electrical resistance is considerably elevated, which causes some troubles, for example, the bioelectrical signal thus output picks up noise, only an unstable record can be obtained, or no record can be obtained in some cases. When the surface of a living body is electrically stimulated via an electrode, the high resistance at the contact area brings about an increase in the current density and thus causes damages such as burn to the living body.

To solve these problems, conductive compositions in the form of liquid, jelly or gel are generally employed in biological electrodes so as to reduce the skin resistance between the living body and the electrode element. These conductive compositions contain a large amount of water and/or electrolytes such as NaCl or KCl which are externally absorbed by the skin horny layer to thereby reduce the skin resistance. Owing to the characteristics of the components, however, such a conductive composition per se has a low viscosity and a high flowability, which makes it difficult to stably sustain the conductive composition between the electrode element and the skin for a prolonged period of time. Thus the electrode element should be provided with a containment space or a holding means such as sponge for supporting the conductive composition. The electrode element should be further provided with an adhesive tape for fixing it on the skin surface. When an adhesive tape is used, however, repeated application and removal of the electrode element cause mechanical damage to the skin.

When an electrode element is applied to the skin surface for a long time via such a conductive composition in an ICU, Holter's electrocardiography, etc., the conductive composition bears mechanical load due to body motion and external pressure. The conductive composition leaks from the electrode element to cause detachment of the electrode element or unstable contact of the electrode element with the skin, thus making it impossible to record the biological signals.

In addition, such a conductive composition is dried during application due to the evaporation of the moisture contained therein. Thus the skin resistance is elevated, thereby making the record of the biological signals unstable. Furthermore, the evaporation of the moisture contained in the conductive composition causes an increase in the chlorine ion concentration in the conductive composition, which induces skin irritation. After the removal of the electrode element, furthermore, such a conductive composition remains on the skin and causes rash.

There are electrode elements usable repeatedly and so-called disposable ones which are thrown away after being used once. In the former ones, a conductive composition is applied to the skin immediately before use. In the latter ones, on the other hand, a conductive composition has been preliminarily filled or incorporated into the electrode in many cases so that they can be easily applied. In the latter case, therefore, it is required to have a structure that the conductive composition is kept not dried until it is used and to store the conductive composition in an airtight package to thereby prevent it from drying during storage. Accordingly, an electrode element of the latter type should have a complicated structure as a whole with taking the use and storage thereof into consideration.

To solve the above-mentioned problems of the liquid conductive composition, there have been recently proposed solid gel conductive compositions which are not flowable but soft and sticky (cf. JP-B-62-44933, JP-B-63-43646, JP-B-63-59334 and JP-B-2-32892; the term "JP-B" as used herein means an "examined published Japanese patent application"). Since stickiness can be imparted to a solid gel conductive composition per se, it can be advantageously employed in a biological electrode without using any adhesive tape for fixation which is essentially required in electrodes with the conventional liquid conductive compositions.

However, the largest disadvantage of these solid gel conductive compositions resides in that they cannot sufficiently reduce the impedance between the electrode and the skin.

The solid gel conductive composition functions to reduce the impedance of the horny layer by allowing the horny layer to absorb the moisture and electrolytes such as KCl or NaCl contained in the conductive composition. In general, moisture contained in a solid gel includes free water which can freely move and bonding water which cannot freely move. The free water largely contributes to the reduction of the impedance of the horny layer. Thus a conductive composition with a larger content of free water can achieve the better effect. However an increase in the free water content might result in the oozing of water onto the solid gel surface or loss of the stickiness, thus damaging the functions characteristic to solid gels.

Conventional solid gels frequently contain polyhydric alcohols such as glycerol and propylene glycol as a plasticizer. Such a plasticizer is nonionic and does not participate in conductivity, which elevates the electrical resistance of the conductive composition per se containing the plasticizer.

To lower the electrical resistance, electrolytes such as KCl and NaCl are added to the conductive composition. It is furthermore required to add water thereto so as to facilitate the smooth migration of these electrolytes. When the moisture content is increased so as to facilitate the smooth migration of the electrolytes, however, the composition suffers from a decrease in the stickiness and thus becomes unusable, as described above. In addition, the percutaneous absorption of excessive moisture or electrolytes causes skin disorders such as rash. Namely, there is the upper limit of the moisture content and thus the impedance of the conductive composition against the skin cannot be sufficiently lowered by this method.

SUMMARY OF THE INVENTION

An object of the present invention is to provide a conductive composition for a biological electrode capable of elevating the moisture content in the horny layer and lowering the impedance between the electrode and the skin while causing little irritation without depending on any increase in the moisture content or the amount of electrolytes.

Thus, the present invention provides a conductive gel composition for a biological electrode which functions to electrically and physically connect a living body to an electrode element and comprises at least the following components: (1) a radical-polymerizable unsaturated compound; (2) a moisturizer serving as a plasticizer and having a function of supplementing and promoting the physiological humidifying function of the skin horny layer; (3) a polymerization initiator; and (4) a crosslinking agent.

The present invention also provides a conductive gel composition for a biological electrode comprises a plasticizer selected from the group consisting of polyhydric alcohols, amines and ethers, as well as the above-described components (1)–(4).

Figure 1:
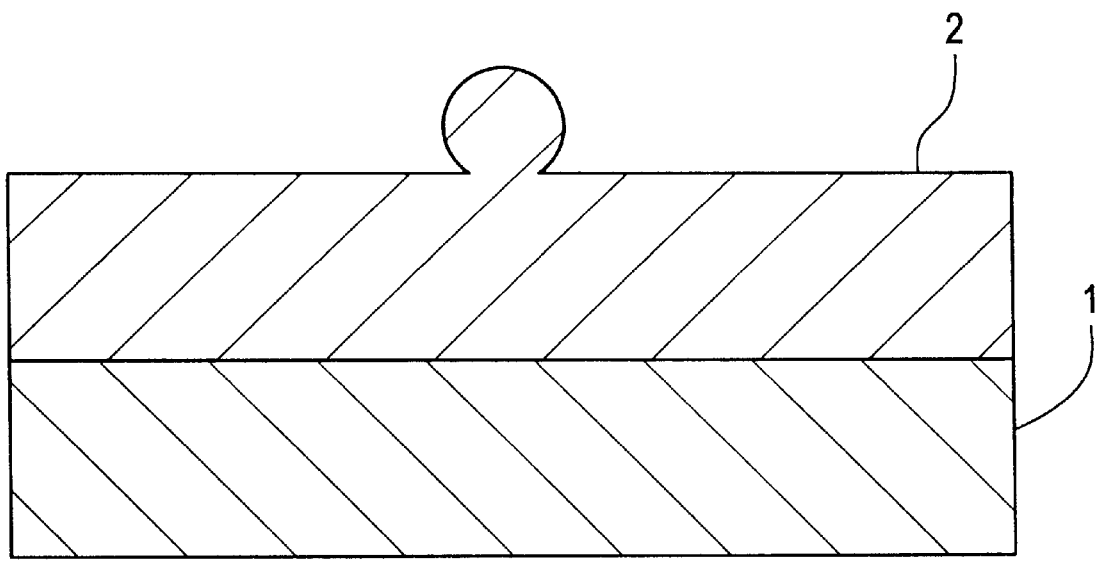
FIG. 1 shows an example of the embodiment in which a conductive composition is employed as a part of an electrode.

1: a conductive composition; and
2: an electrode element.

DETAILED DESCRIPTION OF THE INVENTION

The radical-polymerizable unsaturated compound used in the conductive composition for a biological electrode of the present invention is selected from the group consisting of acrylic acid, methacrylic acid, crotonic acid, itaconic acid, acrylamide, methacrylamide, 2-acrylamido-2-methylpropanesulfonic acid or salts thereof, acrylic acid and vinylpyrrolidone for making a copolymer, vinyl acetate and ethylene for making a copolymer and vinyl acetate and dioctyl maleate for making a copolymer.

These highly polymerizable unsaturated compounds make it possible to easily perform the polymerization.

Examples of the moisturizer include urea, sodium pyrrolidonecarboxylate, sodium lactate, potassium pyrrolidonecarboxylate, potassium lactate and a combination thereof.

Also, lactic acid or pyrrolidonecarboxylic acid can be used in place of potassium lactate, sodium lactate, sodium pyrrolidonecarboxylate and potassium pyrrolidonecarboxylate because the addition of these compounds results in the formation of the same substances as shown in the following reaction schemes 1 and 2. The moisturizer can be used alone or in a combination of two or more thereof.

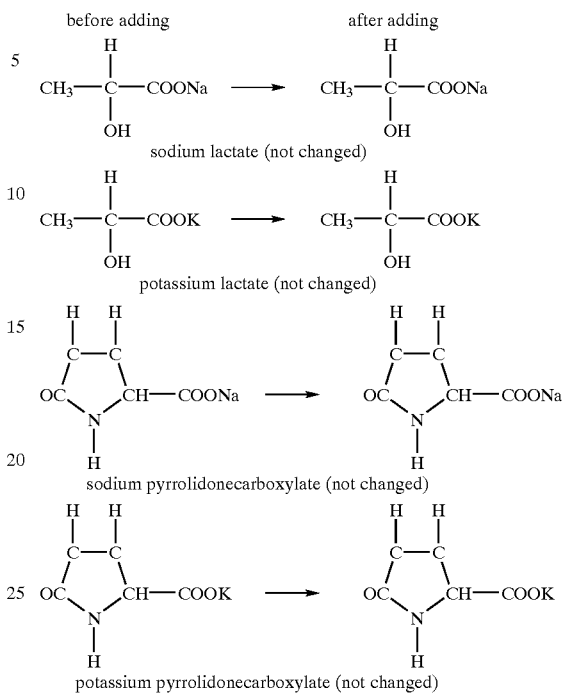

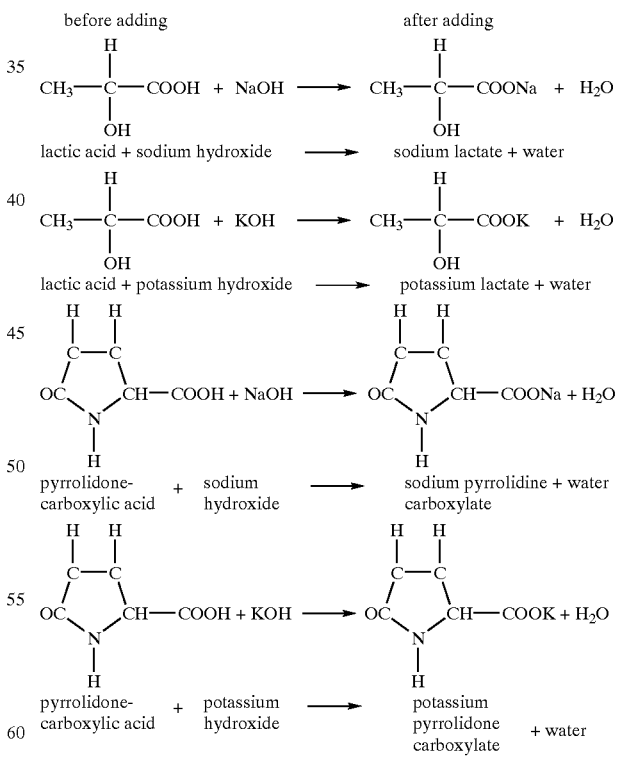

The moisturizer is used in an amount of from 1 to 25% by weight in case of urea, from 1 to 50% by weight in case of sodium pyrrolidonecarboxylate, from 1 to 40% by weight in case of sodium lactate, from 1 to 50% by weight in case of potassium pyrrolidonecarboxylate and from 1 to 50% by weight in case of potassium lactate. Gelation is not inhibited within these ranges of the amount of the moisturizers. In other words, the composition sets to gel using the above-described amount of the moisturizer.

The moisturizer has a plasticizing performance comparable to polyhydric alcohols such as glycerol.

When the moisturizer penetrates into the skin horny layer, water contained in the horny layer tissue binds to the moisturizer to elevate the humidifying function of the whole horny layer. Thus the moisture content in the horny layer can be elevated without externally supplying any moisture. The electrical resistance of the horny layer is reduced as the moisture in the horny layer increases, and thus the impedance of the electrode to the skin lowers.

As described above, the moisturizer contributes to the reduction of the impedance to the skin. Thus the moisture content of the conductive composition can be minimized and thus its stickiness can be improved. The composition of the present invention is free from evaporation of the moisture during storage or use. No means is necessary to prevent evaporation. Further, this conductive composition does not cause the problems such as loss of stickiness due to the oozing of water nor skin disorders caused by the percutaneous absorption of excessive water or electrolytes.

Since the moisturizer used in the present invention is an ionic substance, such as sodium pyrrolidonecarboxylate, potassium pyrrolidonecarboxylate, potassium lactate or sodium lactate, the conductivity can be elevated without adding any electrolytes such as NaCl or KCl, different from the cases with the use of nonionic polyhydric alcohols.

The moisturizer employed in the present invention also has an effect of imparting stickiness. Thus, the stickiness of the composition to the skin can be further improved. In addition, the stickiness to the skin can be arbitrarily controlled easily by varying the content of the moisturizer.

As described above, the moisturizer has four functions as a plasticizer, an electrolyte, an agent for increasing the moisture content in the horny layer and an agent of imparting stickiness. Thus it is the most desirable material as a conductive composition for a biological electrode. Since such a moisturizer is contained in the horny layer inherently, the addition thereof scarcely causes any skin irritation.

As the polymerization initiator, either a photopolymerization initiator or a heat polymerization initiator can be used.

Examples of the photopolymerization initiator include benzyldimethylketal, 1-hydroxycyclohexyl phenyl ketone, an eutectic mixture of 1-hydroxycyclohexyl phenyl ketone with benzophenone, 2-methyl-1-[4-(methylthio)phenyl]-2-morpholinopropanone-1,2-benzyl-2-dimethylamino-1-(4-morpholinophenyl)-butanone-1,2-hydroxy-2-methyl-1-phenyl-propan-1-one, a mixture of 2-hydroxy-2-methyl-1-phenyl-propan-1-one with 2,4,6-trimethylbenzoyldiphenylphosphine oxide, a mixture of 2-hydroxy-2-methyl-1-phenylpropan-1-one with bisacylphosphine oxide, 1-[4-(2-hydroxyethoxy)phenyl]-2-hydroxy-2-methyl-1-propan-1-one and bis(cyclopentadienyl)-bis(2,6-difluoro-3-(pyr-1-yl)titanium.

Examples of the heat polymerization initiator include azobisisobutyronitrile, benzoyl peroxide, lauroyl peroxide, methyl ethyl ketone peroxide, cyclohexanone peroxide, t-butyl hydroperoxide, di-t-butyl peroxide, di-t-amyl peroxide, dicumyl peroxide and t-butyl perbenzoate.

When the composition contains the photopolymerization initiator, the composition undergoes polymerization by irradiation to light. When the composition contains the heat polymerization initiator, it undergoes polymerization by exposing it to heat.

The crosslinking agent is selected from the group consisting of N,N'-methylenebisacrylamide, ethylene glycol dimethacrylate, polyethylene glycol 400 diacrylate, diethylene glycol diacrylate, 1,3-butanediol diacrylate, 1,4-butanediol diacrylate, 1,6-hexanediol diacrylate, neopentylglycol diacrylate, neopentyl glycol diacryl hydroxypivalate, trimethylolpropane triacrylate, pentaerythritol triacrylate, dipentaerythritol hexaacrylate and trimethylolpropane trimethacrylate.

The conductive composition of the present invention may further contain plasticizer to achieve an appropriate flexibility.

Examples of the plasticizer include glycerol, diglycerol, propylene glycol, butylene glycols, amylene glycols, 1,5-pentanediol, trimethylolethane, dipropylene glycol, polypropylene glycol, polyethylene glycol, polyoxyethylene, polyoxypropylene glycol, polyoxypropylene butyl ether, alkylsulfuric acid triethanolamine, diethanolamine, triethanolamine, aminoalkylpropanols, alkyltrimethylammonium chlorides, fatty acid diethanolamides, sorbitan alkyl ethers, sorbitan polyoxyethylene alkyl ethers, dimethylalkylbetaines. These plasticizer may be used alone or in a combination of two or more thereof.

When the conductive composition of the present invention containing the above-described components (1)–(4) is contacted with the skin, the moisturizer acts on the skin horny layer so as to supplement and promote the physiological humidifying function of the horny layer. When an electrode element is applied onto the skin via this conductive composition, the impedance between the electrode element and the skin is lowered due to the moisture in the horny layer thus increased. The moisturizer contained in this composition also serves as a plasticizer.

The conductive composition of the present invention can be prepared, for example, in the following manner.

An unsaturated compound, a crosslinking agent and a polymerization initiator are added to a glass container. Then, a moisturizer is added thereto. A plasticizer may also be added in this instance. Thereafter, water or an aqueous solution of KCl or NaCl is added to the container. An aqueous solution of KOH or NaOH is further added under cooling so that the temperature of the mixture does not exceed 60° C. The resulting mixture is put into a silicone mold having such a size as a diameter of 28 mm and a thickness of 1.5 mm.

In the case of using a photopolymerization initiator, the mold is irradiated with an ultraviolet light using a UV irradiator such as a high pressure mercury lamp (output: 450 W, irradiation distance: 180 mm) for a period that crosslinking polymerization is sufficiently carried out. The UV irradiation may be carried out in a nitrogen atmosphere.

In the case of using a heat polymerization initiator, the mold is heated at a constant temperature in a thermal reactor for a period that crosslinking polymerization is sufficiently carried out. The heat polymerization may be carried out in a nitrogen atmosphere.

The following examples illustrate the present invention in more detail, but are not to be construed to limit the scope of the invention.

EXAMPLE 1

To 27.72% by weight of acrylic acid were added 0.14% by weight of N,N'-methylenebisacrylamide, 0.14% by weight of benzyldimethylketal, 41% by weight of potassium lactate, 13% by weight of water and 18% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky solid gel conductive composition was obtained.

EXAMPLE 2

To 25.78% by weight of acrylic acid were added 0.11% by weight of N,N'-methylenebisacrylamide, 0.11% by weight of benzyldimethylketal, 45% by weight of potassium lactate, 13% by weight of water and 16% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky solid gel conductive composition was obtained.

EXAMPLE 3

To 35.7% by weight of acrylic acid were added 0.15% by weight of N,N'-methylenebisacrylamide, 0.15% by weight of benzyldimethylketal, 20% by weight of urea, 22% by weight of water and 22% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky solid gel conductive composition was obtained.

EXAMPLE 4

To 29.72% by weight of acrylic acid were added 0.14% by weight of N,N'-methylenebisacrylamide, 0.14% by weight of benzyldimethylketal, 39% by weight of potassium lactate, 13% by weight of water and 18% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

Comparative Example 1

To 22% by weight of acrylic acid were added 0.09% by weight of N,N'-methylenebisacrylamide, 0.09% by weight of benzyldimethylketal, 51.82% by weight of glycerol, 13% by weight of water and 13% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

Comparative Example 2

To 30% by weight of water were added 8% by weight of NaOH, 34% by weight of 2-acrylamido-2-methylpropanesulfonic acid, 3% by weight of propylene glycol, 4% by weight of diluted hydrochloric acid, 20.78% by weight of glycerol, 0.04% by weight of N,N'-methylenebisacrylamide and 0.18% by weight of 2% benzoin ethyl ether. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

Comparative Example 3

To 21.82% by weight of acrylic acid were added 0.09% by weight of N,N'-methylenebisacrylamide, 0.09% by weight of benzyldimethylketal, 52% by weight of sodium pyrrolidonecarboxylate (PCA), 13% by weight of water and 13% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. The conductive composition thus obtained was in the form of not a gel but a liquid.

Comparative Example 4

To 21.82% by weight of acrylic acid were added 0.09% by weight of N,N'-methylenebisacrylamide, 0.09% by weight of benzyldimethylketal, 52% by weight of sodium lactate, 13% by weight of water and 13% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. The conductive composition thus obtained was in the form of not a gel but a liquid.

Comparative Example 5

To 21.82% by weight of acrylic acid were added 0.09% by weight of N,N'-methylenebisacrylamide, 0.09% by weight of benzyldimethylketal, 52% by weight of potassium pyrrolidonecarboxylate (PCA), 13% by weight of water and 13% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. The conductive composition thus obtained was in the form of not a gel but a liquid.

Comparative Example 6

To 21.82% by weight of acrylic acid were added 0.09% by weight of N,N'-methylenebisacrylamide, 0.09% by weight of benzyldimethylketal, 52% by weight of potassium lactate, 13% by weight of water and 13% by weight of KOH. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. The conductive composition thus obtained was in the form of not a gel but a liquid.

EXAMPLE 5

To 20% by weight of acrylic acid were added 0.08% by weight of N,N'-methylenebisacrylamide, 0.08% by weight of benzyldimethylketal, 45.84% by weight of glycerol, 12% by weight of KOH, 12% by weight of water and 10% by weight of urea. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 6

To 20% by weight of acrylic acid were added 0.08% by weight of N,N'-methylenebisacrylamide, 0.08% by weight of benzyldimethylketal, 43.84% by weight of glycerol, 12% by weight of KOH, 12% by weight of water and 12% by weight of sodium pyrrolidonecarboxylate (PCA). After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 7

To 20% by weight of acrylic acid were added 0.08% by weight of N,N'-methylenebisacrylamide, 0.08% by weight of benzyldimethylketal, 43.84% by weight of glycerol, 12% by weight of KOH, 12% by weight of water and 12% by weight of sodium lactate. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 8

To 17% by weight of acrylic acid were added 0.07% by weight of N,N'-methylenebisacrylamide, 0.07% by weight of benzyldimethylketal, 42.86% by weight of glycerol, 10% by weight of KOH, 10% by weight of water and 20% by weight of urea. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 9

To 18% by weight of acrylic acid were added 0.08% by weight of N,N'-methylenebisacrylamide, 0.08% by weight of benzyldimethylketal, 44.84% by weight of glycerol, 11% by weight of KOH, 11% by weight of water and 15% by weight of sodium pyrrolidonecarboxylate (PCA). After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 10

To 18% by weight of acrylic acid were added 0.08% by weight of N,N'-methylenebisacrylamide, 0.08% by weight of benzyldimethylketal, 44.84% by weight of glycerol, 11% by weight of KOH, 11% by weight of water and 15% by weight of sodium lactate. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 11

To 20% by weight of acrylic acid were added 0.08% by weight of N,N'-methylenebisacrylamide, 0.08% by weight of benzyldimethylketal, 45.84% by weight of glycerol, 12% by weight of KOH, 12% by weight of water and 10% by weight of potassium pyrrolidonecarboxylate (PCA). After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 12

To 20% by weight of acrylic acid were added 0.08% by weight of N,N'-methylenebisacrylamide, 0.08% by weight of benzyldimethylketal, 45.84% by weight of glycerol, 12% by weight of KOH, 12% by weight of water and 10% by weight of potassium lactate. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 13

To 16% by weight of acrylic acid were added 0.07% by weight of N,N'-methylenebisacrylamide, 0.07% by weight of benzyldimethylketal, 38.86% by weight of glycerol, 10% by weight of KOH, 10% by weight of water and 25% by weight of urea. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

EXAMPLE 14

To 22% by weight of acrylic acid were added 0.09% by weight of N,N'-methylenebisacrylamide, 0.09% by weight of benzyldimethylketal, 25.82% by weight of glycerol, 13% by weight of KOH, 13% by weight of water and 26% by weight of sodium pyrrolidonecarboxylate (PCA). After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

Comparative Example 7

To 17% by weight of acrylic acid were added 0.07% by weight of N,N'-methylenebisacrylamide, 0.07% by weight of benzyldimethylketal, 42.86% by weight of glycerol, 10% by weight of KOH, and 30% by weight of water. After homogeneously dissolving, the resulting mixture was put into a silicone mold having a diameter of 28 mm and a thickness of 1.5 mm and irradiated by an ultraviolet light using a high pressure mercury lamp (output: 450 W, irradiation distance: 180 mm) for 15 seconds to thereby perform crosslinking polymerization. Thus a sticky conductive composition in the form of a solid gel was obtained.

Table 1 shows the composition and properties of each of the conductive compositions of Examples 1 to 14 and Comparative Examples 1 to 7. Regarding the characteristic items, "gelation" means whether each product was in the form of a gel appropriate as a conductive composition or not (A: yes, X: no); "weight change at room temperature" means the degree of moisture evaporation determined after allowing each composition in a room for a definite period of time (expressed in a change in wt. % after 24 hours); "stickiness to skin" means the force (g/20 mm) required for peeling off each conductive composition which had been molded into a strip (thickness: 1.5 mm, width: 20 mm) by using a mold different from the silicone molds employed above and applied onto the skin; "moisture content in horny layer" means the moisture content [expressed in conductance ($\mu$S)] in the horny layer measured after a definite period of time (30 minutes) following the application of each conductive composition to the skin for a certain period of time (1 hour) and then peeling it off; and "impedance to skin" means the impedance (expressed in k$\Omega$, at 10 Hz) determined when an electrode element 2 was applied to the skin via each conductive composition 1 employed as a part of the electrode as shown in FIG. 1.

TABLE 1-1

| Composition (wt. %) | Comp. Ex. 1 | Comp. Ex. 2 | Ex. 1 | Ex. 2 | Ex. 3 | Comp. Ex. 3 |
|---|---|---|---|---|---|---|
| N,N'-methylenebisacrylamide | 0.09 | 0.04 | 0.14 | 0.11 | 0.15 | 0.09 |
| benzyldimethylketal | 0.09 | — | 0.14 | 0.11 | 0.15 | 0.09 |
| acrylic acid monomer | 22 | — | 27.72 | 25.78 | 35.7 | 21.82 |
| glycerol | 51.82 | 20.78 | — | — | — | — |
| KOH | 13 | — | 18 | 16 | 22 | 13 |
| water | 13 | 30 | 13 | 13 | 22 | 13 |
| NaOH | — | 8 | — | — | — | — |
| urea | — | — | — | — | 20 | — |
| sodium PCA | — | — | — | — | — | 52 |
| sodium lactate | — | — | — | — | — | — |
| potassium PCA | — | — | — | — | — | — |
| potassium lactate | — | — | 41 | 45 | — | — |
| propylene glycol | — | 3 | — | — | — | — |
| acidic AMPS powder | — | 34 | — | — | — | — |
| diluted hydrochloric acid | — | 4 | — | — | — | — |
| 2% benzoin ethyl ether | — | 0.18 | — | — | — | — |
| Characteristics | | | | | | |
| gelation | A | A | A | A | A | X |
| weight change at room temp. (%) | 0 | −16 | +4 | +8 | −2 | — |
| stickiness to skin (g/20 mm) | 38 | 79 | 274 | 286 | 23 | — |
| moisture content in horny layer ($\mu$S) | 107 | 80 | 357 | 244 | 154 | — |
| impedance to skin (k$\Omega$, at 10 Hz) | 220 | 207 | 29 | 25 | 53 | — |

| Composition (wt. %) | Comp. Ex. 4 | Comp. Ex. 5 | Comp. Ex. 6 | Ex. 4 |
|---|---|---|---|---|
| N,N'-methylenebisacrylamide | 0.09 | 0.09 | 0.09 | 0.14 |
| benzyldimethylketal | 0.09 | 0.09 | 0.09 | 0.14 |
| acrylic acid monomer | 21.82 | 21.82 | 21.82 | 29.72 |
| glycerol | — | — | — | — |
| KOH | 13 | 13 | 13 | 18 |
| water | 13 | 13 | 13 | 13 |
| NaOH | — | — | — | — |
| urea | — | — | — | — |
| sodium PCA | — | — | — | — |
| sodium lactate | 52 | — | — | — |
| potassium PCA | — | 52 | — | — |
| potassium lactate | — | — | 52 | 39 |
| propylene glycol | — | — | — | — |
| acidic AMPS powder | — | — | — | — |
| diluted hydrochloric acid | — | — | — | — |
| 2% benzoin ethyl ether | — | — | — | — |

TABLE 1-1-continued

| Characteristics | | | | |
|---|---|---|---|---|
| gelation | X | X | X | A |
| weight change at room temp. (%) | — | — | — | +3 |
| stickiness to skin (g/20 mm) | — | — | — | 292 |
| moisture content in horny layer ($\mu$S) | — | — | — | 270 |
| impedance to skin (k$\Omega$, at 10 Hz) | — | — | — | 16 |

TABLE 1-2

| Composition (wt. %) | Comp. Ex. 7 | Ex. 5 | Ex. 6 | Ex. 7 | Ex. 8 |
|---|---|---|---|---|---|
| N,N'-methylenebisacrylamide | 0.07 | 0.08 | 0.08 | 0.08 | 0.07 |
| benzyldimethylketal | 0.07 | 0.08 | 0.08 | 0.08 | 0.07 |
| acrylic acid monomer | 17 | 20 | 20 | 20 | 17 |
| glycerol | 42.86 | 45.84 | 43.84 | 43.84 | 42.86 |
| KOH | 10 | 12 | 12 | 12 | 10 |
| water | 30 | 12 | 12 | 12 | 10 |
| urea | — | 10 | — | — | 20 |
| sodium PCA | — | — | 12 | — | — |
| sodium lactate | — | — | — | 12 | — |
| potassium PCA | — | — | — | — | — |
| potassium lactate | — | — | — | — | — |
| Characteristics | | | | | |
| gelation | A | A | A | A | A |
| weight change at room temp. (%) | −20 | 0 | 0 | 0 | +1 |
| stickiness to skin (g/20 mm) | 0 | 81 | 228 | 217 | 115 |
| moisture content in horny layer ($\mu$S) | 70 | 107 | 221 | 167 | 223 |
| impedance to skin (k$\Omega$, at 10 Hz) | 185 | 133 | 88 | 82 | 129 |

| Composition (wt. %) | Ex. 9 | Ex. 10 | Ex. 11 | Ex. 12 | Ex. 13 | Ex. 14 |
|---|---|---|---|---|---|---|
| N,N'-methylenebisacrylamide | 0.08 | 0.08 | 0.08 | 0.08 | 0.07 | 0.09 |
| benzyldimethylketal | 0.08 | 0.08 | 0.08 | 0.08 | 0.07 | 0.09 |
| acrylic acid monomer | 18 | 18 | 20 | 20 | 16 | 22 |
| glycerol | 44.84 | 44.84 | 45.84 | 45.84 | 38.86 | 25.82 |
| KOH | 11 | 11 | 12 | 12 | 10 | 13 |
| water | 11 | 11 | 12 | 12 | 10 | 13 |
| urea | — | — | — | — | 25 | — |
| sodium PCA | 15 | — | — | — | — | 26 |
| sodium lactate | — | 15 | — | — | — | — |
| potassium PCA | — | — | 10 | — | — | — |
| potassium lactate | — | — | — | 10 | — | — |
| Characteristics | | | | | | |
| gelation | A | A | A | A | A | A |
| weight change at room temp. (%) | +1 | +1 | +2 | +1 | +1 | +3 |
| stickiness to skin (g/20 mm) | 239 | 137 | 172 | 206 | 132 | 213 |
| moisture content in horny layer ($\mu$S) | 196 | 211 | 189 | 239 | 144 | 298 |
| impedance to skin (k$\Omega$, at 10 Hz) | 88 | 75 | 93 | 78 | 139 | 39 |

As Table 1 indicates, the products of Examples 1 to 14 are each in the form of an appropriate gel, without suffering from moisture loss after allowing it to stand at room temperature, has a large stickiness to the skin, gives a high moisture content in the horny layer and shows an extremely low impedance to the skin. In particular, the products of Examples 1, 2 and 4 to 14 are superior in the characteristics to those of Comparative Examples 1 to 7. That is to say, conductive compositions containing a moisturizer are much more suitable as a conductive composition for a biological electrode than those containing no moisturizer.

Table 2 shows the results of experiments which were performed to determine the appropriate content (% by weight) of a moisturizer in a conductive composition for a biological electrode. Each of the test products S1 to S30 was prepared in the same manner as those of Examples 1 to 3 using the definite amount (% by weight) of the components listed in Table 2. The results shown in Table 2 revealed that the appropriate amount of the moisturizers, i.e., urea, sodium pyrrolidonecarboxylate, sodium lactate, potassium pyrrolidonecarboxylate and potassium lactate, are respectively from 1 to 25% by weight, from 1 to 50% by weight, from 1 to 40% by weight, from 1 to 50% by weight and from 1 to 50% by weight. The use of each moisturizer in an amount smaller than the lower limit as defined above could achieve no effect. On the other hand, the use of each moisturizer in an amount exceeding the upper limit as defined above failed to cause appropriate gelation.

TABLE 2-1

| Composition (wt. %) | Test product | S1 | S2 | S3 | S4 | S5 |
|---|---|---|---|---|---|---|
| | moisturizer (%) | 1 | 1 | 1 | 1 | 1 |
| N,N'-methylenebisacrylamide | | 0.19 | 0.19 | 0.19 | 0.19 | 0.19 |
| benzyldimethylketal | | 0.19 | 0.19 | 0.19 | 0.19 | 0.19 |
| acrylic acid monomer | | 44.62 | 44.62 | 44.62 | 44.62 | 44.62 |
| KOH | | 27 | 27 | 27 | 27 | 27 |
| water | | 27 | 27 | 27 | 27 | 27 |
| urea | | 1 | — | — | — | — |
| sodium PCA | | — | 1 | — | — | — |
| sodium lactate | | — | — | 1 | — | — |
| potassium PCA | | — | — | — | 1 | — |
| potassium lactate | | — | — | — | — | 1 |
| Characteristics | | | | | | |
| gelation | | A | A | A | A | A |
| weight change at room temp. (%) | | — | — | — | — | — |
| stickiness to skin (g/20 mm) | | — | — | — | — | — |
| moisture content in horny layer ($\mu S$) | | — | — | — | — | — |
| impedance to skin (k$\Omega$, at 10 Hz) | | — | — | — | — | — |

| Composition (wt. %) | Test product | S6 | S7 | S8 | S9 | S10 |
|---|---|---|---|---|---|---|
| | moisturizer (%) | 25 | 50 | 40 | 50 | 50 |
| N,N'-methylenebisacrylamide | | 0.14 | 0.09 | 0.11 | 0.09 | 0.09 |
| benzyldimethylketal | | 0.14 | 0.09 | 0.11 | 0.09 | 0.09 |
| acrylic acid monomer | | 34.72 | 23.82 | 27.78 | 23.82 | 23.82 |
| KOH | | 20 | 13 | 16 | 13 | 13 |
| water | | 20 | 13 | 16 | 13 | 13 |
| urea | | 25 | — | — | — | — |
| sodium PCA | | — | 50 | — | — | — |
| sodium lactate | | — | — | 40 | — | — |
| potassium PCA | | — | — | — | 50 | — |
| potassium lactate | | — | — | — | — | 50 |
| Characteristics | | | | | | |
| gelation | | A | A | A | A | A |
| weight change at room temp. (%) | | −2 | −2 | 0 | +3 | −1 |
| stickiness to skin (g/20 mm) | | 89 | 142 | 158 | 167 | 170 |
| moisture content in horny layer ($\mu S$) | | 183 | 249 | 230 | 317 | 492 |
| impedance to skin (k$\Omega$, at 10 Hz) | | 110 | 36 | 45 | 25 | 14 |

| Composition (wt. %) | Test product | S11 | S12 | S13 | S14 | S15 |
|---|---|---|---|---|---|---|
| | moisturizer (%) | 30 | 60 | 50 | 60 | 60 |
| N,N'-methylenebisacrylamide | | 0.13 | 0.08 | 0.09 | 0.08 | 0.08 |
| benzyldimethylketal | | 0.13 | 0.08 | 0.09 | 0.08 | 0.08 |
| acrylic acid monomer | | 31.74 | 17.84 | 23.82 | 17.84 | 17.84 |
| KOH | | 19 | 11 | 13 | 11 | 11 |
| water | | 19 | 11 | 13 | 11 | 11 |
| urea | | 30 | — | — | — | — |
| sodium PCA | | — | 60 | — | — | — |
| sodium lactate | | — | — | 50 | — | — |
| potassium PCA | | — | — | — | 60 | — |
| potassium lactate | | — | — | — | — | 60 |
| Characteristics | | | | | | |
| gelation | | X | X | X | X | X |
| weight change at room temp. (%) | | — | — | — | — | — |
| stickiness to skin (g/20 mm) | | — | — | — | — | — |
| moisture content in horny layer ($\mu S$) | | — | — | — | — | — |
| impedance to skin (k$\Omega$, at 10 Hz) | | — | — | — | — | — |

TABLE 2-2

| Composition (wt. %) | Test product | S16 | S17 | S18 | S19 | S20 |
|---|---|---|---|---|---|---|
| | moisturizer (%) | 1 | 1 | 1 | 1 | 1 |
| N,N'-methylenebisacrylamide | | 0.09 | 0.09 | 0.09 | 0.09 | 0.09 |
| benzyldimethylketal | | 0.09 | 0.09 | 0.09 | 0.09 | 0.09 |
| acrylic acid monomer | | 21 | 21 | 21 | 21 | 21 |
| Glycerol | | 51.82 | 51.82 | 51.82 | 51.82 | 51.82 |
| KOH | | 13 | 13 | 13 | 13 | 13 |
| water | | 13 | 13 | 13 | 13 | 13 |
| urea | | 1 | — | — | — | — |
| sodium PCA | | — | 1 | — | — | — |
| sodium lactate | | — | — | 1 | — | — |
| potassium PCA | | — | — | — | 1 | — |
| potassium lactate | | — | — | — | — | 1 |
| Characteristics | | | | | | |
| gelation | | A | A | A | A | A |
| weight change at room temp. (%) | | +1 | −1 | 0 | +2 | +1 |
| stickiness to skin (g/20 mm) | | 59 | 56 | 52 | 83 | 42 |
| moisture content in horny layer ($\mu S$) | | 189 | 265 | 215 | 153 | 233 |
| impedance to skin (k$\Omega$, at 10 Hz) | | 240 | 180 | 73 | 150 | 150 |

| Composition (wt. %) | Test product | S21 | S22 | S23 | S24 | S25 |
|---|---|---|---|---|---|---|
| | moisturizer (%) | 25 | 50 | 40 | 50 | 50 |
| N,N'-methylenebisacrylamide | | 0.07 | 0.09 | 0.11 | 0.09 | 0.09 |
| benzyldimethylketal | | 0.07 | 0.09 | 0.11 | 0.09 | 0.09 |
| acrylic acid monomer | | 16 | 22.82 | 26.78 | 22.82 | 22.82 |
| Glycerol | | 10 | 13 | 16 | 13 | 13 |
| KOH | | 10 | 13 | 16 | 13 | 13 |
| water | | 10 | 13 | 16 | 13 | 13 |
| urea | | 25 | — | — | — | — |
| sodium PCA | | — | 50 | — | — | — |
| sodium lactate | | — | — | 40 | — | — |
| potassium PCA | | — | — | — | 50 | — |
| potassium lactate | | — | — | — | — | 50 |
| Characteristics | | | | | | |
| gelation | | A | A | A | A | A |
| weight change at room temp. (%) | | 0 | 0 | 0 | +3 | +1 |
| stickiness to skin (g/20 mm) | | 81 | 228 | 217 | 180 | 216 |
| moisture content in horny layer ($\mu S$) | | 107 | 221 | 167 | 178 | 229 |
| impedance to skin (k$\Omega$, at 10 Hz) | | 153 | 88 | 82 | 97 | 81 |

| Composition (wt. %) | Test product | S26 | S27 | S28 | S29 | S30 |
|---|---|---|---|---|---|---|
| | moisturizer (%) | 30 | 60 | 50 | 60 | 60 |
| N,N'-methylenebisacrylamide | | 0.13 | 0.08 | 0.09 | 0.08 | 0.08 |
| benzyldimethylketal | | 0.13 | 0.08 | 0.09 | 0.08 | 0.08 |
| acrylic acid monomer | | 30.74 | 16.84 | 22.82 | 16.84 | 16.84 |
| Glycerol | | 1 | 1 | 1 | 1 | 1 |
| KOH | | 19 | 11 | 13 | 11 | 11 |
| water | | 19 | 11 | 13 | 11 | 11 |
| urea | | 30 | — | — | — | — |
| sodium PCA | | — | 60 | — | — | — |
| sodium lactate | | — | — | 50 | — | — |
| potassium PCA | | — | — | — | 60 | — |
| potassium lactate | | — | — | — | — | 60 |
| Characteristics | | | | | | |
| gelation | | X | X | X | X | X |
| weight change at room temp. (%) | | — | — | — | — | — |
| stickiness to skin (g/20 mm) | | — | — | — | — | — |
| moisture content in horny layer ($\mu S$) | | — | — | — | — | — |
| impedance to skin (k$\Omega$, at 10 Hz) | | — | — | — | — | — |

In Examples 1 to 14 shown in Table 1 and the test products S1 to S30 shown in Table 2, acrylic acid was employed as the radical-polymerizable unsaturated compound. However, similar effects can be achieved by substituting the acrylic acid by another radical-polymerizable unsaturated compound selected from methacrylic acid, crotonic acid, itaconic acid, acrylamide, methacrylamide, 2-acrylamido-2-methylpropanesulfonic acid or salts thereof, etc., acrylic acid/vinylpyrrolidone copolymer, vinyl acetate/ethylene copolymer and vinyl acetate/dioctyl maleate copolymer.

Similarly, benzyldimethylketal was employed as the polymerization initiator capable of inducing photopolymerization. However, similar effects can be achieved by substituting the benzyldimethylketal by another polymerization initiator selected from among 1-hydroxy-cyclohexyl phenyl ketone, an eutectic mixture of 1-hydroxy-cyclohexyl phenyl ketone with benzophenone, 2-methyl-1-[4-(methylthio)phenyl]-2-morpholinopropanone-1,2-benzyl-2-dimethylamino-1-(4-morpholinophenyl)-butanone-1,2-hydroxy-2-methyl-1-phenylpropan-1-one, a mixture of 2-hydroxy-2-methyl-1-phenyl-propan-1-one with 2,4,6-trimethylbenzoyldiphenyl-phosphine oxide, a mixture of 2-hydroxy-2-methyl-1-phenylpropan-1-one with bisacylphosphine oxide, 1-[4-(2-hydroxyethoxy)phenyl]-2-hydroxy-2-methyl-1-propan-1-one and bis(cyclopentadienyl)-bis(2,6-difluoro-3-(pyr-1-yl)titanium.

In the above examples, the composition was produced by photopolymerization. However, it is also possible to produce the composition by heat polymerization. In such a case, examples of a polymerization initiator to be used include azobisisobutyronitrile, benzoyl peroxide, lauroyl peroxide, methyl ethyl ketone peroxide, cyclohexanone peroxide, t-butyl hydroperoxide, di-t-butyl peroxide, di-t-amyl peroxide, dicumyl peroxide and t-butyl perbenzoate. The compositions thus produced are comparable in the effects to those obtained by photopolymerization.

Also, N,N'-methylenebis-acrylamide which is a radical-polymerizable and highly reactive unsaturated compound was used in the above examples as the crosslinking agent. However, it is possible to substitute N,N'-methylenebisacrylamide by another radical-polymerizable highly reactive unsaturated compound selected from among ethylene glycol dimethacrylate, polyethylene glycol 400 diacrylate, diethylene glycol diacrylate, 1,3-butanediol diacrylate, neopentylglycol diacrylate, neopentyl glycol diacryl hydroxypivalate, trimethylolpropane triacrylate, pentaerythritol triacrylate, dipentaerythritol hexaacrylate and trimethylolpropane trimethacrylate to thereby achieve similar effects.

Also, glycerol was used as the plasticizer in the above examples. However, it is possible to substitute the glycerol by another plasticizer selected from diglycerol, propylene glycol, butylene glycols, amylene glycols, 1,5-pentanediol, trimethylolethane, dipropylene glycol, polypropylene glycol, polyethylene glycol, polyoxyethylene, polyoxypropylene glycol, polyoxypropylene butyl ether, alkylsulfuric acid triethanolamine, diethanolamine, triethanolamine, aminoalkylpropanols, alkyltrimethylammonium chlorides, fatty acid diethanolamides, sorbitan alkyl ethers, sorbitan polyoxyethylene alkyl ethers, dimethylalkylbetaines and a combination of two or more thereof to thereby achieve similar functions and effects.

TEST EXAMPLE

A device for eliminating ventricular fibrillation is sometimes employed in the treatment of ventricular fibrillation, etc. In such a case, it is necessary to take an electrocardiogram at the same time so as to confirm the effects immediately after the treatment. There are some cases that the electrocardiogram cannot be accurately taken due to the material or conductive composition of the electrode element employed. When the device for eliminating ventricular fibrillation is used, a partial electric current passes between the electrodes for electrocardiography and thus polarization voltage generates, which tentatively causes a large and rapid change in the direct-current voltage. To solve this problem, it is necessary to use an unpolarized electrode such as Ag/AgCl or AgCl for the electrode element. To induce this unpolarizing effect, it is furthermore necessary that the conductive composition contacted with the electrode element contains Cl ion commonly used in the electrode element.

Table 3 shows the polarization voltages generating in the compositions of Examples 3 and 8 and the compositions of the Examples 15 and 16 having the same compositions as Examples 3 and 8, respectively, except for further containing 0.7% by weight of KCl, based on the whole composition, under passing a current of 0.5 $\mu$A. Thus, it can be found that the polarization voltage can be sufficiently lowered when KCl is added to the conductive composition of the present invention as shown in Table 3.

TABLE 3

| Example | 3 | 15 | 8 | 16 |
|---|---|---|---|---|
| KCl added (wt. %) | 0 | 0.7 | 0 | 0.7 |
| polarization voltage (mV) at 0.5 $\mu$A | 38 | 1 | 38 | 1 |

While the invention has been described in detail and with reference to specific examples thereof, it will be apparent to one skilled in the art that various changes and modifications can be made therein without departing from the spirit and scope thereof.

What is claimed is:

1. A composition comprising at least the following components:

(1) a radical-polymerizable unsaturated compound;

(2) a moisturizer serving as a plasticizer and having a function of supplementing and promoting the physiological humidifying function of the horny layer of a living body;

(3) a polymerization initiator; and (4) a crosslinking agent;

wherein said composition is a gel, and wherein said moisturizer is urea present in an amount of from 10 to 25% by weight based on the total weight of the composition, and wherein the composition is capable of electrically and physically connecting the living body to an electrode element.

2. The composition as claimed in claim 1, wherein said unsaturated compound is selected from the group consisting of acrylic acid, methacrylic acid, crotonic acid, itaconic acid, acrylamide, methacrylamide, 2-acrylamido-2-methylpropanesulfonic acid or salts thereof, acrylic acid and vinylpyrrolidone for making a copolymer, vinyl acetate and ethylene for making a copolymer and vinyl acetate and dioctyl maleate for making a copolymer.

3. The composition as claimed in claim 1, wherein said polymerization initiator is a photopolymerization initiator initiating polymerization with light or a heat polymerization initiator initiating polymerization with heat.

4. The composition as claimed in claim 3, wherein said photopolymerization initiator is selected from the group consisting of benzyldimethylketal, 1-hydroxycyclohexyl phenyl ketone, an eutectic mixture of 1-hydroxycyclohexyl phenyl ketone with benzophenone, 2-methyl-1-[4-(methylthio)phenyl]-2-morpholinopropanone-1,2-benzyl-2-dimethylamino-1-(4-morpholinophenyl)-butanone-1,2-hydroxy-2-methyl-1-phenylpropan-1-one, a mixture of 2-hydroxy-2-methyl-1-phenylpropan-1-one with 2,4,6-trimethylbenzoyldiphenylphosphine oxide, a mixture of 2-hydroxy-2-methyl-1-phenylpropan-1-one with bisacylphosphine oxide, 1-[4-(2-hydroxyethoxy)-phenyl]-2- hydroxy-2-methyl-1-propan-1-one and bis(cyclopentadienyl)-bis(2,6-difluoro-3-(pyr-1-yl)titanium.

5. The composition as claimed in claim 3, wherein said heat polymerization initiator is selected from the group consisting of azobisisobutyronitrile, benzoyl peroxide, lauroyl peroxide, methyl ethyl ketone peroxide, cyclohexanone peroxide, t-butyl hydroperoxide, di-t-butyl peroxide, di-t-amyl peroxide, dicumyl peroxide and t-butyl perbenzoate.

6. The composition as claimed in claim 1, wherein said crosslinking agent is selected from the group consisting of N,N'-methylenebisacrylamide, ethylene glycol dimethacrylate, polyethylene glycol 400 diacrylate, diethylene glycol diacrylate, 1,3-butanediol diacrylate, 1,4-butanediol diacrylate, 1,6-hexanediol diacrylate, neopentylglycol diacrylate, neopentyl glycol diacryl hydroxypivalate, trimethylolpropane triacrylate, pentaerythritol triacrylate, dipentaerythritol hexaacrylate and trimethylolpropane trimethacrylate.

7. The composition as claimed in claim 1, which further contains at least one electrolyte selected from the group consisting of potassium chloride and sodium chloride.

8. A composition comprising at least the following components:
    (1) a radical-polymerizable unsaturated compound;
    (2) a plasticizer selected from the group consisting of polyhydric alcohols, amines and ethers;
    (3) a moisturizer serving as a plasticizer and having a function of supplementing and promoting the physiological humidifying function of the horny layer of skin of a living body;
    (4) a polymerization initiator; and
    (5) a crosslinking agent;
    wherein said composition is a gel, and
    wherein said moisturizer is urea in an amount of from 10 to 25% by weight based on the total weight of the composition, and
    wherein the composition is capable of electrically and physically connecting the living body to an electrode element.

9. The composition as claimed in claim 8, wherein said unsaturated compound is selected from the group consisting of acrylic acid, methacrylic acid, crotonic acid, itaconic acid, acrylamide, methacrylamide, 2-acrylamido-2-methylpropanesulfonic acid or salts thereof, an acrylic acid/vinylpyrrolidone mixture, a vinyl acetate/ethylene mixture and a vinyl acetate/dioctyl maleate mixture.

10. The composition as claimed in claim 8, wherein said plasticizer is selected from the group consisting of glycerol, diglycerol, propylene glycol, butylene glycols, amylene glycols, 1,5-pentanediol, trimethylolethane, dipropylene glycol, polypropylene glycol, polyethylene glycol, polyoxyethylene, polyoxypropylene glycol, polyoxypropylene butyl ether, alkylsulfuric acid triethanolamine, diethanolamine, triethanolamine, aminoalkylpropanols, alkyltrimethylammonium chlorides, fatty acid diethanolamides, sorbitan alkyl ethers, sorbitan polyoxyethylene alkyl ethers, dimethylalkylbetaines and a combination of two or more thereof.

11. The composition claimed in claim 8, wherein said polymerization initiator is a photopolymerization initiator or a heat polymerization initiator.

12. The composition as claimed in claim 11, wherein said photopolymerization initiator is selected from the group consisting of benzyldimethylketal, 1-hydroxycyclohexyl phenyl ketone, an eutectic mixture of 1-hydroxycyclohexyl phenyl ketone with benzophenone, 2-methyl-1-[4-(methylthio)phenyl]-2-morpholinopropanone-1,2-benzyl-2-dimethylamino-1-(4-morpholinophenyl)-butanone-1,2-hydroxy-2-methyl-1-phenylpropan-1-one, a mixture of 2-hydroxy-2-methyl-1-phenylpropan-1-one with 2,4,6-trimethylbenzoyldiphenylphosphine oxide, a mixture of 2-hydroxy-2-methyl-1-phenylpropan-1-one with bisacylphosphine oxide, 1-[4-(2-hydroxyethoxy)phenyl]-2-hydroxy-2-methyl-1-propan-1-one and bis(cyclopentadienyl)-bis(2,6-difluoro-3-(pyr-1-yl)titanium.

13. The composition as claimed in claim 11, wherein said heat polymerization initiator is selected from the group consisting of azobisisobutyronitrile, benzoyl peroxide, lauroyl peroxide, methyl ethyl ketone peroxide, cyclohexanone peroxide, t-butyl hydroperoxide, di-t-butyl peroxide, di-t-amyl peroxide, dicumyl peroxide and t-butyl perbenzoate.

14. The composition as claimed in claim 8, wherein said crosslinking agent is selected from the group consisting of N,N'-methylenebisacrylamide, ethylene glycol dimethacrylate, polyethylene glycol 400 diacrylate, diethylene glycol diacrylate, 1,3-butanediol diacrylate, 1,4-butanediol diacrylate, 1,6-hexanediol diacrylate, neopentylglycol diacrylate, neopentyl glycol diacryl hydroxypivalate, trimethylolpropane triacrylate, pentaerythritol triacrylate, dipentaerythritol hexaacrylate and trimethylolpropane trimethacrylate.

15. The composition as claimed in claim 8, which further contains at least one electrolyte selected from the group consisting of potassium chloride and sodium chloride.

* * * * *